US011229352B2

(12) United States Patent
Ito

(10) Patent No.: US 11,229,352 B2
(45) Date of Patent: Jan. 25, 2022

(54) INSTRUMENT INSERTION ASSISTING TOOL

(71) Applicant: Olympus Corporation, Hachioji (JP)

(72) Inventor: Yoshiaki Ito, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 563 days.

(21) Appl. No.: 16/161,819

(22) Filed: Oct. 16, 2018

(65) Prior Publication Data
US 2019/0046019 A1 Feb. 14, 2019

Related U.S. Application Data

(63) Continuation of application No. PCT/JP2017/010441, filed on Mar. 15, 2017.

(30) Foreign Application Priority Data

Apr. 18, 2016 (JP) .............................. JP2016-083081

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00087* (2013.01); *A61B 1/00096* (2013.01);
(Continued)

(58) Field of Classification Search
None
See application file for complete search history.

(56) References Cited

U.S. PATENT DOCUMENTS 6,096,009 A * 8/2000 Windheuser ...... A61M 25/0097
24/339
8,647,256 B2 2/2014 Carrillo, Jr.
(Continued)

FOREIGN PATENT DOCUMENTS

JP 62-152429 7/1987
JP 02-136603 11/1990
(Continued)

OTHER PUBLICATIONS

International Search Report and Written Opinion from corresponding International Application No. PCT/JP2017/010441, dated Jun. 20, 2017.

*Primary Examiner* — Timothy J Neal
(74) *Attorney, Agent, or Firm* — Oliff PLC

(57) ABSTRACT

An instrument insertion assisting tool includes a wire attaching member, a guide piece, and a first engaging member. The wire attaching member is configured to be attached to a manipulator of an endoscope at a position adjacent to a forceps plug and offset from a seal hole of the forceps plug. The forceps plug is attached to a forceps port of the manipulator and has the seal hole through which a wire is inserted. The guide piece projects from the wire attaching member. The guide piece is configured to direct the wire so that a first portion of the wire is directed along a central axis of the seal hole. The first engaging member projects from the wire attaching member. The first engaging member is configured to direct the wire so that a second portion of the wire is directed along the wire attaching member.

17 Claims, 13 Drawing Sheets

(51) Int. Cl.
- *A61B 1/05* (2006.01)
- *A61B 1/005* (2006.01)
- *A61B 1/01* (2006.01)
- *A61B 1/06* (2006.01)

(52) U.S. Cl.
CPC ...... *A61B 1/00133* (2013.01); *A61B 1/00137* (2013.01); *A61B 1/00177* (2013.01); *A61B 1/05* (2013.01); *A61B 1/0057* (2013.01); *A61B 1/01* (2013.01); *A61B 1/0676* (2013.01)

(56) References Cited

U.S. PATENT DOCUMENTS

| | | | |
|---|---|---|---|
| 2003/0073955 A1* | 4/2003 | Otawara | A61B 1/00098 604/164.01 |
| 2004/0015050 A1 | 1/2004 | Goto et al. | |
| 2004/0162465 A1* | 8/2004 | Carrillo | A61M 25/09041 600/104 |
| 2006/0195117 A1 | 8/2006 | Rucker et al. | |
| 2008/0194913 A1 | 8/2008 | Tinkham et al. | |
| 2010/0081878 A1 | 4/2010 | Byers et al. | |
| 2010/0087710 A1 | 4/2010 | Weldon et al. | |

FOREIGN PATENT DOCUMENTS

| | | |
|---|---|---|
| JP | 2002-515305 | 5/2002 |
| JP | 2003-116777 | 4/2003 |
| JP | 2004-180996 | 7/2004 |
| JP | 2006-068550 | 3/2006 |
| JP | 2008-529723 | 8/2008 |
| JP | 4475719 | 3/2010 |
| WO | 1999059664 | 11/1999 |
| WO | 2007086876 | 8/2007 |

\* cited by examiner

INSTRUMENT INSERTION ASSISTING TOOL

CROSS-REFERENCE TO RELATED APPLICATIONS

This application is a continuation application of PCT Application No. PCT/JP2017/010441 filed on Mar. 15, 2017, which in turn claim priority to the Japanese Patent Application No. 2016-083081 filed on Apr. 18, 2016 in Japan which is hereby incorporated by reference in its entirety.

TECHNICAL FIELD

The technology disclosed herein relates to an instrument insertion assisting tool suitable for use with an endoscope including a forceps port for guiding an instrument such as a forceps or the like into the endoscope.

DESCRIPTION OF THE RELATED ART

In recent years, it has been customary to observe and treat a lesion in a gastrointestinal system, a pancreatic biliary duct system, or the like with a so-called side-view-type endoscope (hereinafter referred to simply as "endoscope"). The endoscope includes an observational optical system disposed on a side surface of a distal end portion of an insertion device, e.g., an insertion portion to be inserted into a body of an examinee. Treatments for treating a pancreatic biliary duct system using an endoscope include (i) a diagnostic treatment for imaging a bile duct or pancreatic duct with an endoscope, (ii) an inspection using a biliary endoscope for imaging the inside of a bile duct or a pancreatic duct, and (iii) a curative treatment for collecting gallstones that are present in a common bile duct or the like with a balloon, a gripping treatment instrument, or the like.

In a treatment for a common bile duct, it is necessary to insert and remove a plurality of treatment instruments or instruments such as catheters or the like into and from the bile duct selectively several times. According to such a treatment, it is the usual practice to insert a distal end portion of an endoscopic insertion portion nearly up to the duodenal papilla and then insert a guide wire introduced into a body cavity through a treatment instrument insertion channel into the bile duct under X-ray fluoroscopy. The proximal end side of the guide wire extends out of a treatment instrument insertion port of an endoscope manipulator. While keeping the guide wire inside the bile duct, the proximal end side of the wire guide is inserted into a guide wire lumen defined in a treatment instrument, and the treatment instrument is guided along the guide wire into the bile duct. In this manner, various treatment instruments can selectively be inserted without much effort.

For the purpose of shortening a guide wire to change such treatment instruments efficiently in an operating room, there is known a structure in which a guide wire tubular cavity is restrictively disposed in a distal end portion of a treatment instrument, as disclosed in Japanese Patent Laid-Open No. 2003-116777. Japanese Patent Laid-Open No. 2003-116777 also discloses a technology in which (i) a guide wire locking member is disposed adjacent to a forceps port, and (ii) a guide wire extending from a forceps plug mounted on the forceps port is secured to the guide wire locking member. The purpose of this technology is (i) to eliminate a cooperative process in which a surgeon and a perioperative assistant stay close to each other and (ii) to change treatment instruments with a small number of people in changing treatment instruments using a guide wire.

However, when the guide wire is secured to the guide wire locking member according to the technology disclosed in Japanese Patent Laid-Open No. 2003-116777, since the guide wire extends at a certain angle from the forceps plug toward the guide wire locking member, the guide wire and the treatment instrument extend in different directions. The guide wire and the treatment instrument then tend to spread a hole such as a round hole, a slit, or the like defined in the forceps plug for hermetically sealing the guide wire and the treatment instrument, possibly letting a body fluid such as bile or the like leak out of the forceps plug.

Therefore, there is a need for an instrument insertion assisting tool which is capable of securing a guide wire on a manipulator side while preventing a body fluid from leaking out of a forceps plug.

BRIEF SUMMARY OF EMBODIMENTS

In accordance with an aspect of the present disclosure, an instrument insertion assisting tool for use with an endoscope includes a tube, a forceps port, and a forceps plug. An instrument and a guide wire used for guiding the instrument is inserted into an insertion portion through the tube. The tube is open outwardly on a manipulator through the forceps port. The forceps plug is mounted on the forceps port in closing relation thereto. The forceps plug has a hole through which the instrument and the guide wire extends. The instrument insertion assisting tool includes a plate-shaped wire attaching member, a plate-shaped guide piece, a hook-shaped first engaging member, and a tortuously-shaped second engaging member. The plate-shaped wire attaching member is attached to the manipulator of the endoscope at a position adjacent to the forceps plug and offset from the hole. The plate-shaped guide piece projects from the wire attaching member, for partially controlling a direction along which the guide wire projecting from the forceps plug extends to cause a portion of the guide wire that is positioned immediately after projecting from the forceps plug to extend along a central axis of the hole. The hook-shaped first engaging member projects from the wire attaching member, for engaging the guide wire which extends along the direction controlled by the guide piece. The tortuously-shaped second engaging member engages another portion of the guide wire which is engaged by the first engaging member.

In accordance with another aspect of the present disclosure, an instrument insertion assisting tool includes a wire attaching member, a guide piece, and a first engaging member. The wire attaching member is configured to be attached to a manipulator of an endoscope at a position adjacent to a forceps plug and offset from a seal hole of the forceps plug. The forceps plug is attached to a forceps port of the manipulator and has the seal hole through which a wire is inserted. The guide piece projects from the wire attaching member. The guide piece is configured to direct the wire so that a first portion of the wire is directed along a central axis of the seal hole. The first engaging member projects from the wire attaching member. The first engaging member is configured to direct the wire so that a second portion of the wire is directed along the wire attaching member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Figure 1:
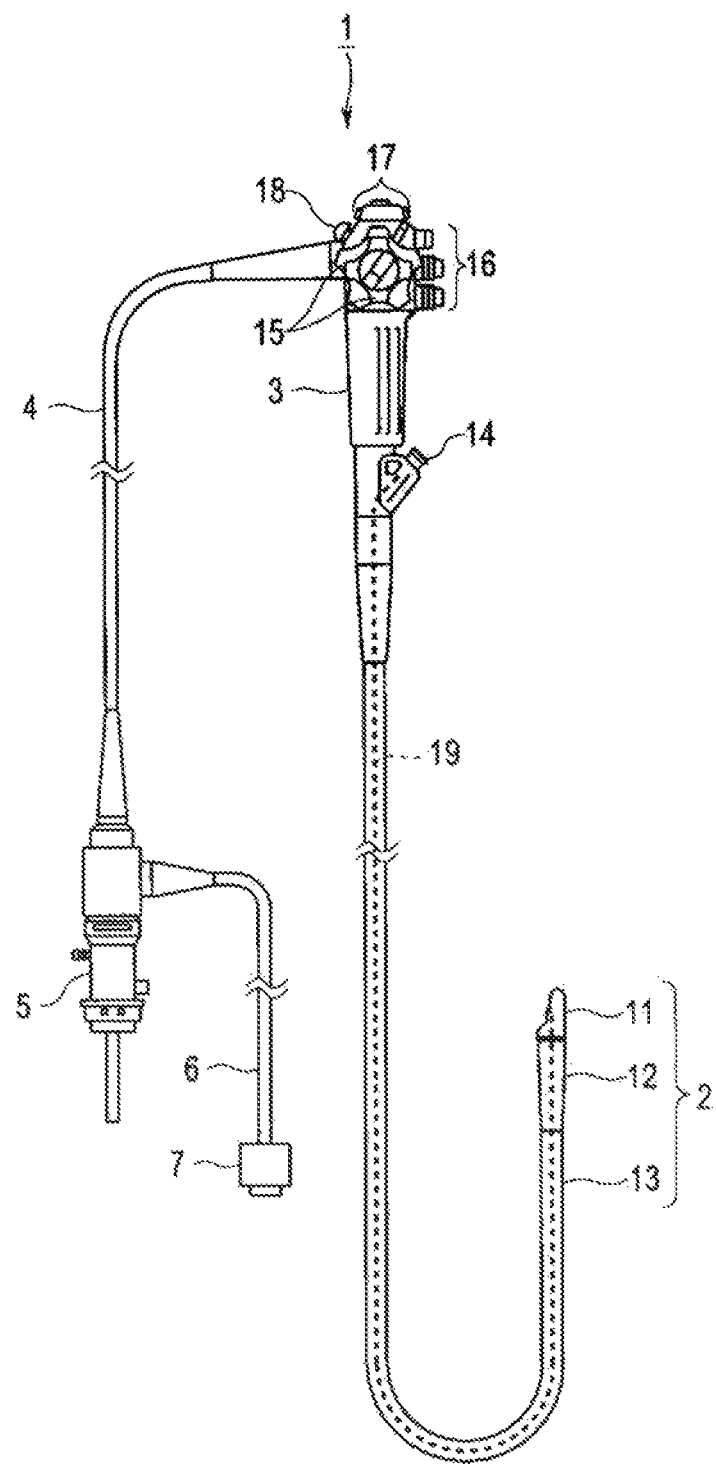
FIG. 1 is a view depicting the structure of an endoscope.
Figure 2:
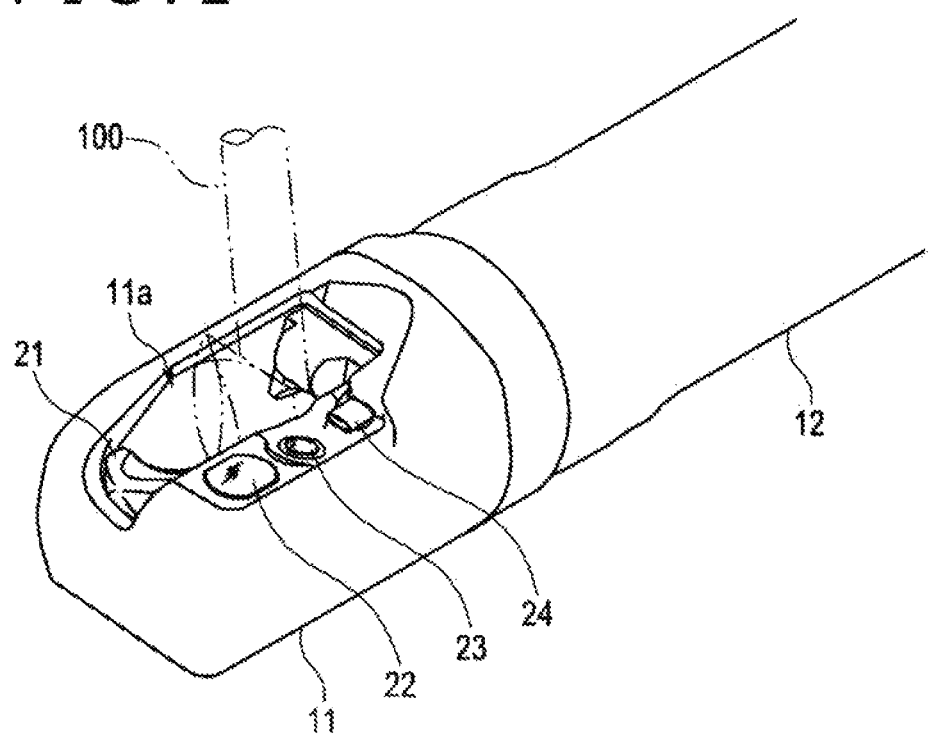
FIG. 2 is a perspective view depicting the structure of a distal end portion of an insertion portion of the endoscope illustrated in FIG. 1.

The general structure of an endoscope 1 according to the present embodiment will first be described hereinafter with reference to FIGS. 1 and 2. The endoscope 1 according to the present embodiment that is illustrated by way of example is configured to optically observe the inside of the body of an examinee and to have a treatment instrument raising base on its distal end. However, the endoscope 1 may be configured to further have an ultrasonic probe on its distal end for scanning the inside of an examinee with an ultrasonic beam to capture an ultrasonic tomographic image of the examinee.

The endoscope 1 mainly includes an insertion portion 2, a manipulator 3, and a universal cord 4. The insertion portion 2 is insertable into the body of the examinee. The manipulator 3 is positioned at a proximal end of the insertion portion 2. The universal cord 4 extends from a side of the manipulator 3. The insertion portion 2 includes a distal-end member 11, a bendable member 12, and a flexible tube 13, all of which are attached to one another. The distal-end member 11 is disposed on its distal end. The bendable member 12 is disposed on a proximal end side of the distal-end member 11. The flexible tube 13 is disposed on a proximal end side of the bendable member 12 and connected to a distal end of the manipulator 3.

The manipulator 3 has a forceps port 14 held in fluid communication with a treatment instrument channel 19 formed as a tube. The manipulator 3 has angled knobs 15, buttons 16, switches 17, and a control lever 18 that are used to control and/or manipulate the insertion portion 2. The angled knobs 15 is for bending the bendable member 12. The fluid delivery buttons 16 are disposed on the distal-end member 11 and are used to control the delivery of fluids from a fluid delivery unit that is not depicted. The switches 17 is defined as a release switch disposed on the distal-end member 11. The control lever 18 is for raising and lowering a treatment instrument raising base 21 (see FIG. 2) disposed on the distal-end member 11.

The treatment instrument raising base 21 is disposed on the distal-end member 11 of the insertion portion 2. The treatment instrument raising base 21 raises and lowers a treatment instrument 100 (see FIG. 2) as an instrument projecting from an opening 11a defined in a side peripheral portion of the distal-end member 11, thereby changing the direction in which the treatment instrument 100 projects. In other words, the endoscope 1 is defined as a side-view-type endoscope. An illumination window 22, an observation window 23, etc. are disposed on the side peripheral portion of the distal-end member 11. The treatment instrument raising base 21 is disposed in the endoscope for raising the treatment instrument 100 into an observational direction. The distal-end member 11 also includes a fluid delivery nozzle 24 mainly for cleaning the observation window 23.

An endoscope connector 5 that is connected to a light source device, not depicted, is connected to a proximal end side of the universal cord 4. Illuminating light is emitted from the light source device, is transmitted through a light guide bundle, and is emitted from the illumination window 22 (see FIG. 2) disposed on the distal-end member 11. The light guide bundle is inserted in the universal cord 4, the manipulator 3, and the insertion portion 2. The endoscope 1 may have a light source such as a light emitting diode (LED) or the like used as an illumination device, disposed on the distal-end member 11.

Figure 11:
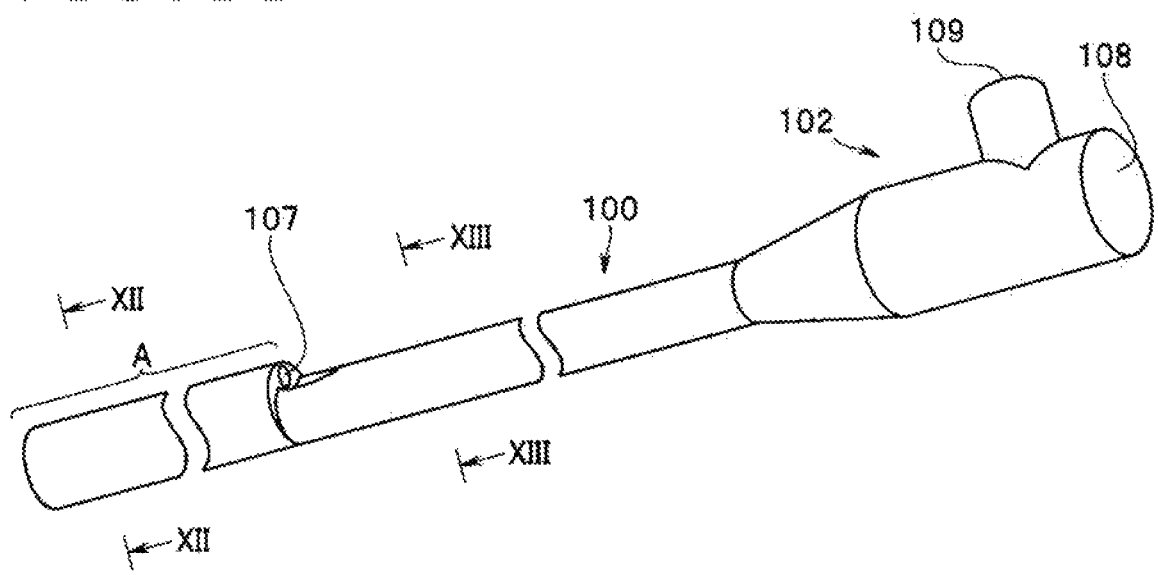
FIG. 11 is a perspective view depicting a treatment instrument by way of example.
Figure 12:
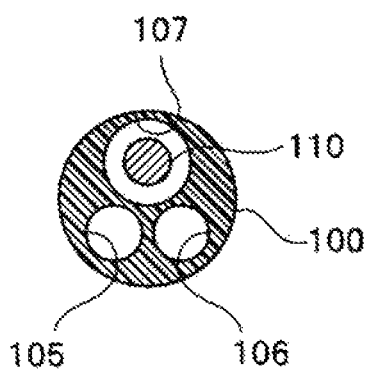
FIG. 12 is a cross-sectional view taken along line XII-XII of FIG. 11.
Figure 13:
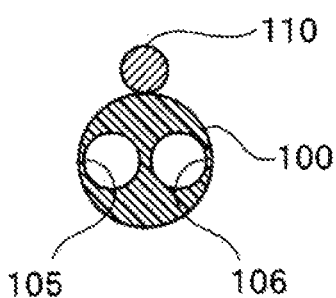
FIG. 13 is a cross-sectional view taken along line XIII-XIII of FIG. 11.
Figure 14:
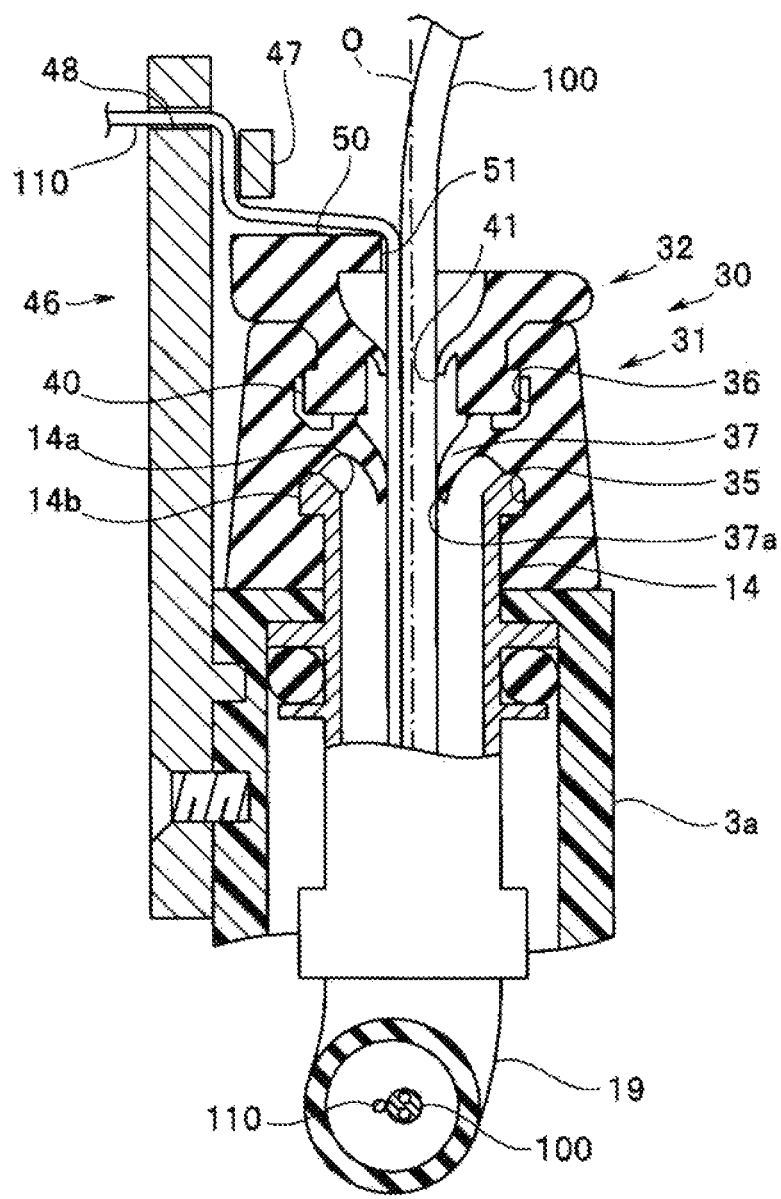
FIG. 14 is a cross-sectional view depicting the manner in which the guide wire projecting from the forceps plug is secured to the wire attaching member according to a first modification.

A video cable 6 extends from the endoscope connector 5, and a video connector 7 is disposed on the end of the video cable 6. The video connector 7 is electrically connected to a camera control unit, not depicted. The camera control unit is electrically connected to an image capturing device disposed in the distal-end member 11 through the video connector 7. The camera control unit is electrically connected to an image display device, not depicted, and outputs an image captured by the image capturing device through the observation window 23 (see FIG. 2) on the distal-end member 11 to the image display device. The treatment instrument 100 for use with the endoscope 1 according to the present embodiment will be described by way of example hereinafter with reference to FIGS. 11 through 13. The treatment instrument 100 depicted in FIGS. 11 through 13 includes a multi-lumen catheter, for example.

The illustrated treatment instrument 100 has an injection lumen 105 and a gas delivery lumen 106, both as lumens defined fully longitudinally (axially) therein from its distal end to its proximal end. The injection lumen is for allowing a contrast medium or the like to flow therein. The treatment instrument 100 also includes a guide wire lumen 107 defined restrictively in a region A on the distal end side of the treatment instrument 100. The guide wire lumen 107 is used as a tubular cavity through which a guide wire 110 to be described hereinafter can be inserted. A treatment instrument manipulator 102 is joined to a proximal end side of the treatment instrument 100. The treatment instrument manipulator 102 includes a liquid delivery port 108 and a gas delivery port 109. The liquid delivery port 108 is held in fluid communication with the injection lumen 105. The gas delivery port 109 is held in fluid communication with the gas delivery lumen 106. In the endoscope 1 of the structure described hereinbefore, as depicted in FIGS. 3 through 7, for example, a forceps plug 30 is removably mounted on the forceps port 14.

The forceps plug 30 is formed to hermetically close a forceps port 14a that is open in the forceps port 14. The forceps plug 30 has a forceps plug body 31 and a lid 32, each formed of an elastic resin or the like. The forceps plug body 31 includes a tubular member that has a substantially barrel-shaped appearance. The forceps plug body 31 has a first circumferential groove 35 defined in an inner circumferential surface thereof at its one end. The forceps port 14 has an outward flange 14b disposed on an outer circumferential surface thereof. The outward flange 14b is fittable in the first circumferential groove 35. When the forceps port 14 is inserted into the one end of the forceps plug body 31 with the first circumferential groove 35 that is elastically fitted over the outward flange 14b, the forceps plug body 31 is hermetically coupled to the forceps port 14. The forceps plug body 31 has a second circumferential groove 36 defined in the inner circumferential surface thereof at its other end. The lid 32 can be fitted in the second circumferential groove 36.

The forceps plug body 31 also has a lip-shaped inward flange 37 disposed circumferentially therein between the first circumferential groove 35 and the second circumferential groove 36. A seal hole 37a is formed in the inward flange 37. The seal hole 37a is disposed in a position that faces the forceps port 14a at the time the forceps plug body 31 is coupled to the forceps port 14. When the treatment instrument 100 and the guide wire 110 are inserted through the seal hole 37a, the edge of the inward flange 37 that forms the seal hole 37a is elastically held in sliding contact with the outer circumferential surfaces of the treatment instrument 100 and the guide wire 110. The lid 32 includes a substantially disk-shaped member attached to the forceps plug body 31 via a joint band 33. The lid 32 is used to hermetically close the forceps port 14a by being placed over the other end of the forceps plug body 31. The lid 32 has an outward flange 40 on one surface thereof which faces the forceps plug body 31 when the lid 32 is placed over the other end of the forceps plug body 31. The outward flange 40 is fittable in the second circumferential groove 36.

The outward flange 40 is inserted in the other end of the forceps plug body 31. When the outward flange 40 is elastically fitted in the second circumferential groove 36, the lid 32 is hermetically attached to the forceps plug body 31. The lid 32 has a slit 41 defined therein at a position that faces the seal hole 37a (and the forceps port 14a) when the lid 32 is joined to the forceps plug body 31. The slit 41 is used as a hole through which the treatment instrument 100 and the guide wire 110 can be inserted. Normally when the treatment instrument 100 and the guide wire 110 are pulled out of the slit 41, the slit 41 is a normally closed slit that hermetically closes the forceps port 14a under elastically restoring forces.

When the treatment instrument 100 and the guide wire 110 are inserted through the slit 41, the slit 41 is spread open by the treatment instrument 100 and the guide wire 110. When the treatment instrument 100 and the guide wire 110 are inserted through the slit 41, the edge of the outward flange 40 that forms the slit 41 is elastically held in sliding contact with the outer circumferential surfaces of the treatment instrument 100 and the guide wire 110. The treatment instrument 100 and the guide wire 110 are inserted through the slit 41 and the seal hole 37a into the forceps port 14a, and then the treatment instrument 100 and the guide wire 110 can reach a desired position in the body of the examinee through the treatment instrument channel 19. Once the guide wire 110 is inserted into the body of the examinee, the guide wire 110 is left to dwell in the body of the examinee until the intended treatment is finished. After the guide wire 110 is left to dwell in the body of the examinee, various treatment instruments 100 are suitably and selectively inserted into and pulled out of the body of the examinee while being guided by the guide wire 110.

Figure 6:
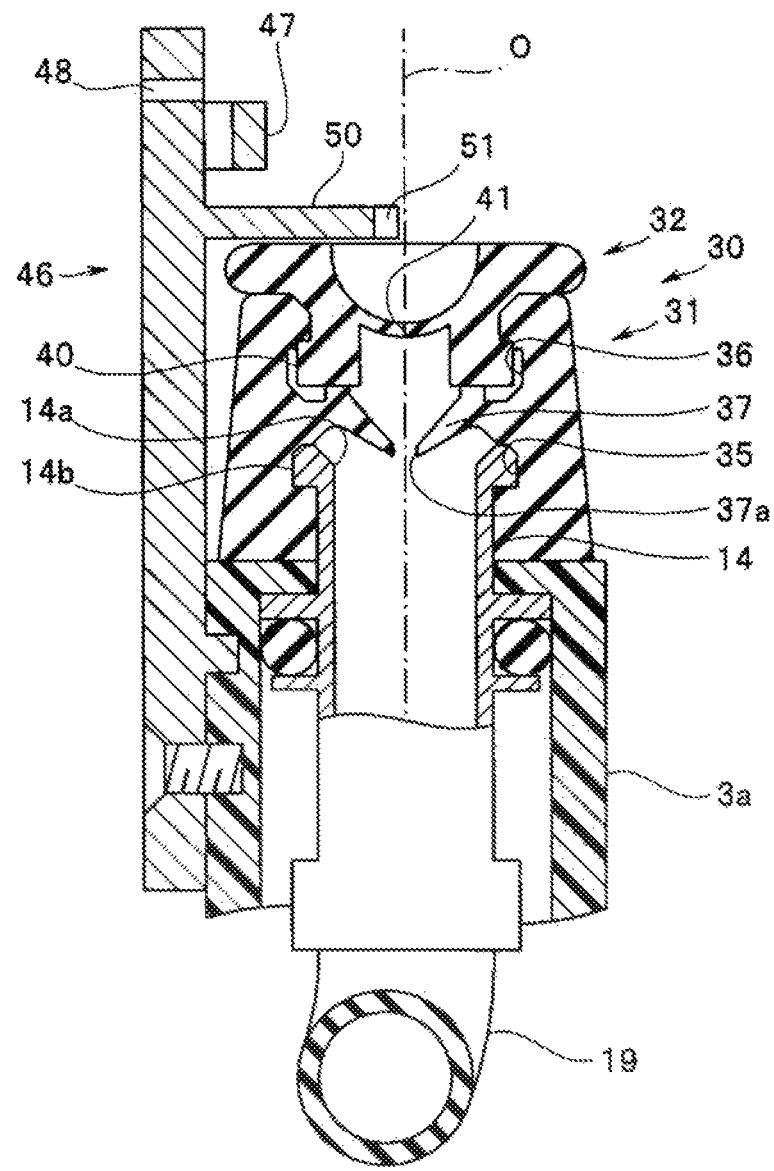
FIG. 6 is a cross-sectional view depicting the portion of the endoscope on which the forceps plug and the wire attaching member are mounted.

A wire attaching member 45 is attached to the manipulator 3 at a position adjacent to the forceps plug 30 for preventing the guide wire 110 from moving longitudinally without asking an assistant or the like for help when the treatment instrument 100 is inserted or pulled out or when treatments are made using various treatment instruments 100. The wire attaching member 45 is formed by a substantially plate-shaped member made of resin. An attaching device 46 is disposed on one end of the wire attaching member 45. The wire attaching member 45 is attached to the manipulator 3 at a position offset from the slit 41 and the seal hole 37a in the forceps plug 30. Specifically, as depicted in FIG. 6, for example, the other end of the wire attaching member 45 is secured by a screw or the like to a mount 3a (a mount on which the forceps port 14 is mounted) that projects from the manipulator 3.

Figure 3:
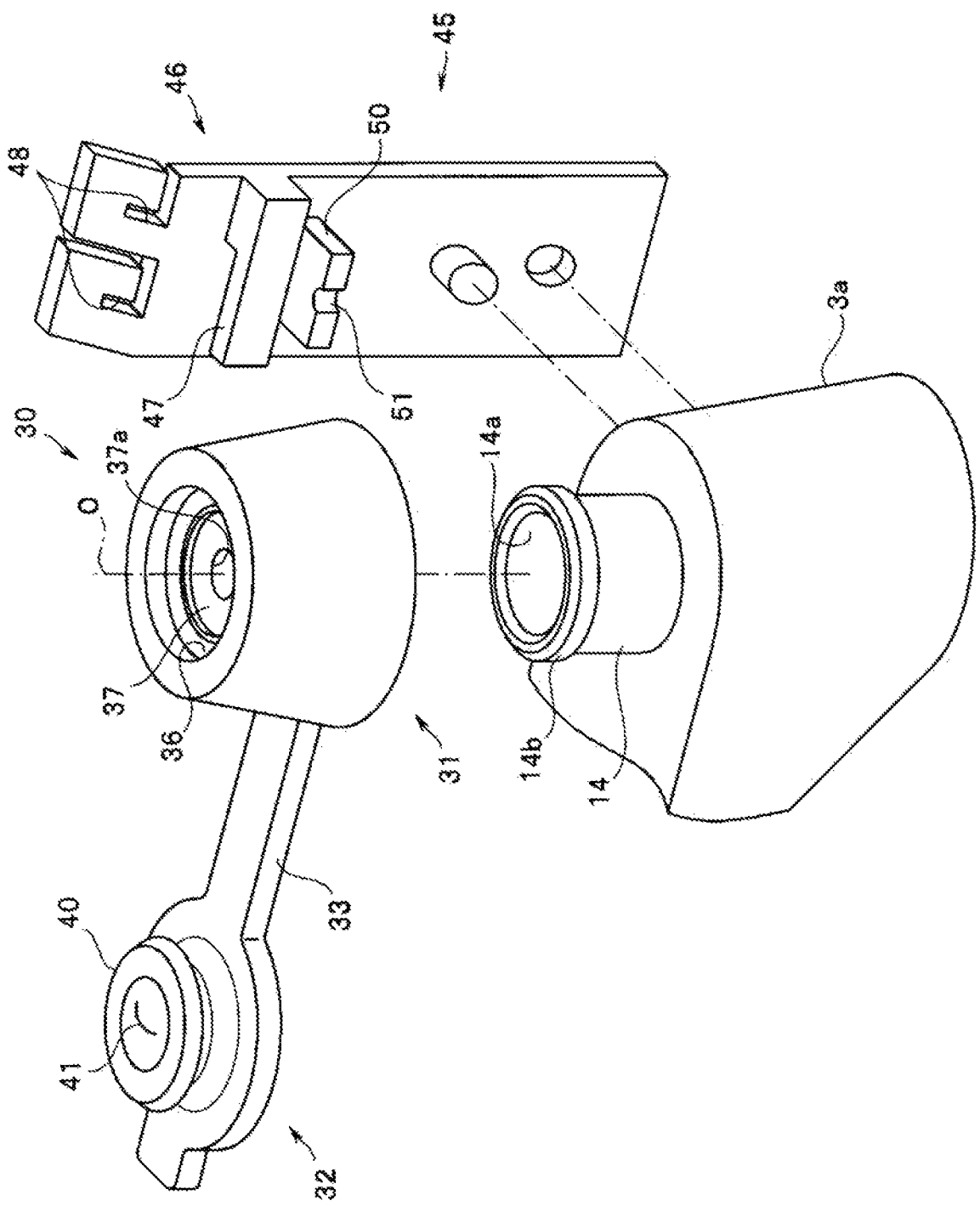
FIG. 3 is a perspective view depicting a forceps plug and a wire attaching member before they are mounted on the endoscope.
Figure 4:
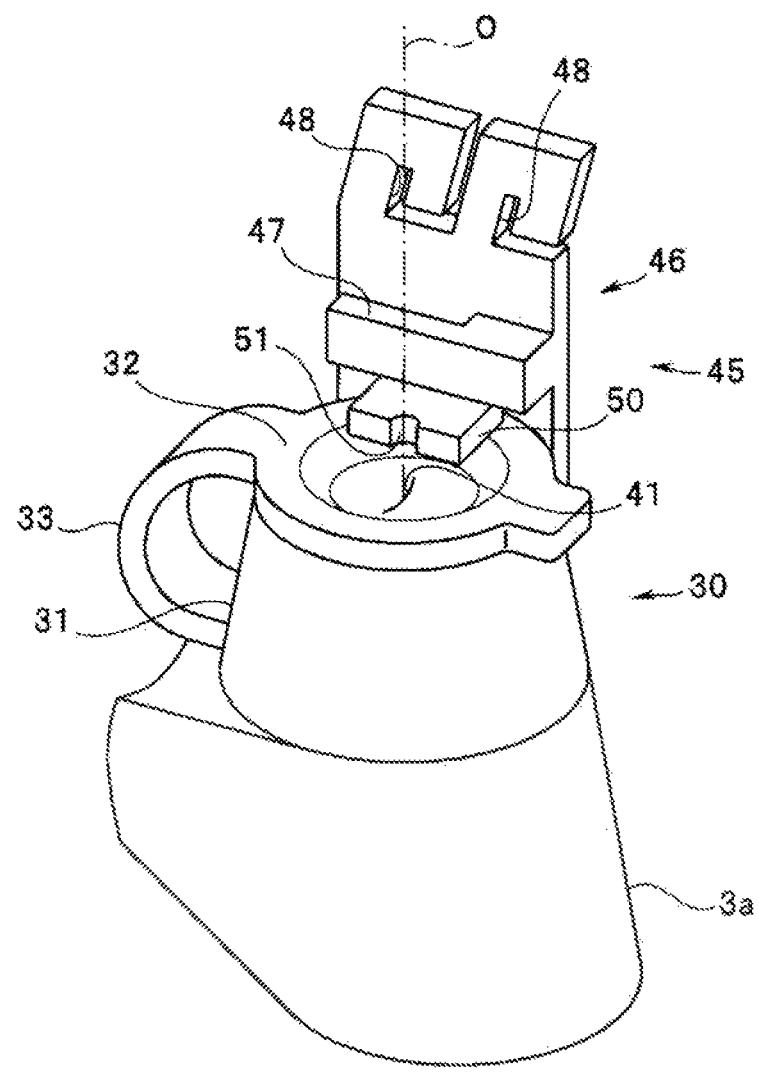
FIG. 4 is a perspective view depicting a portion of the endoscope on which the forceps plug and the wire attaching member are mounted.
Figure 5:
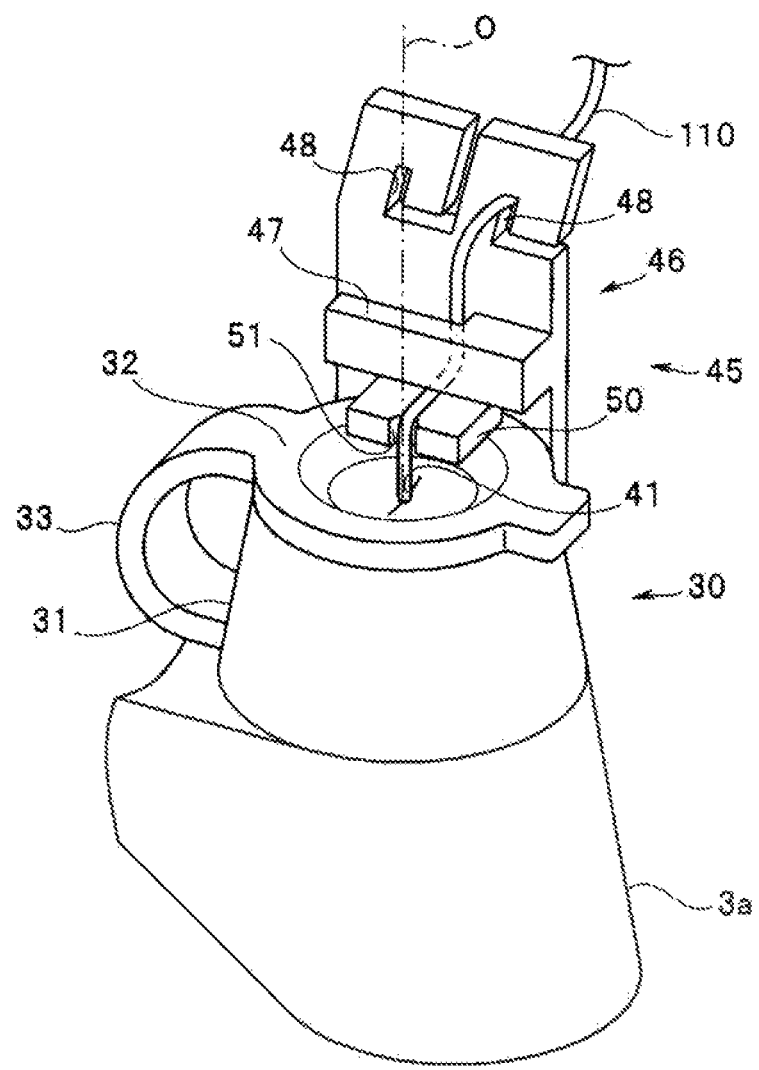
FIG. 5 is a perspective view depicting the manner in which a guide wire projecting from the forceps plug is secured to the wire attaching member.
Figure 7:
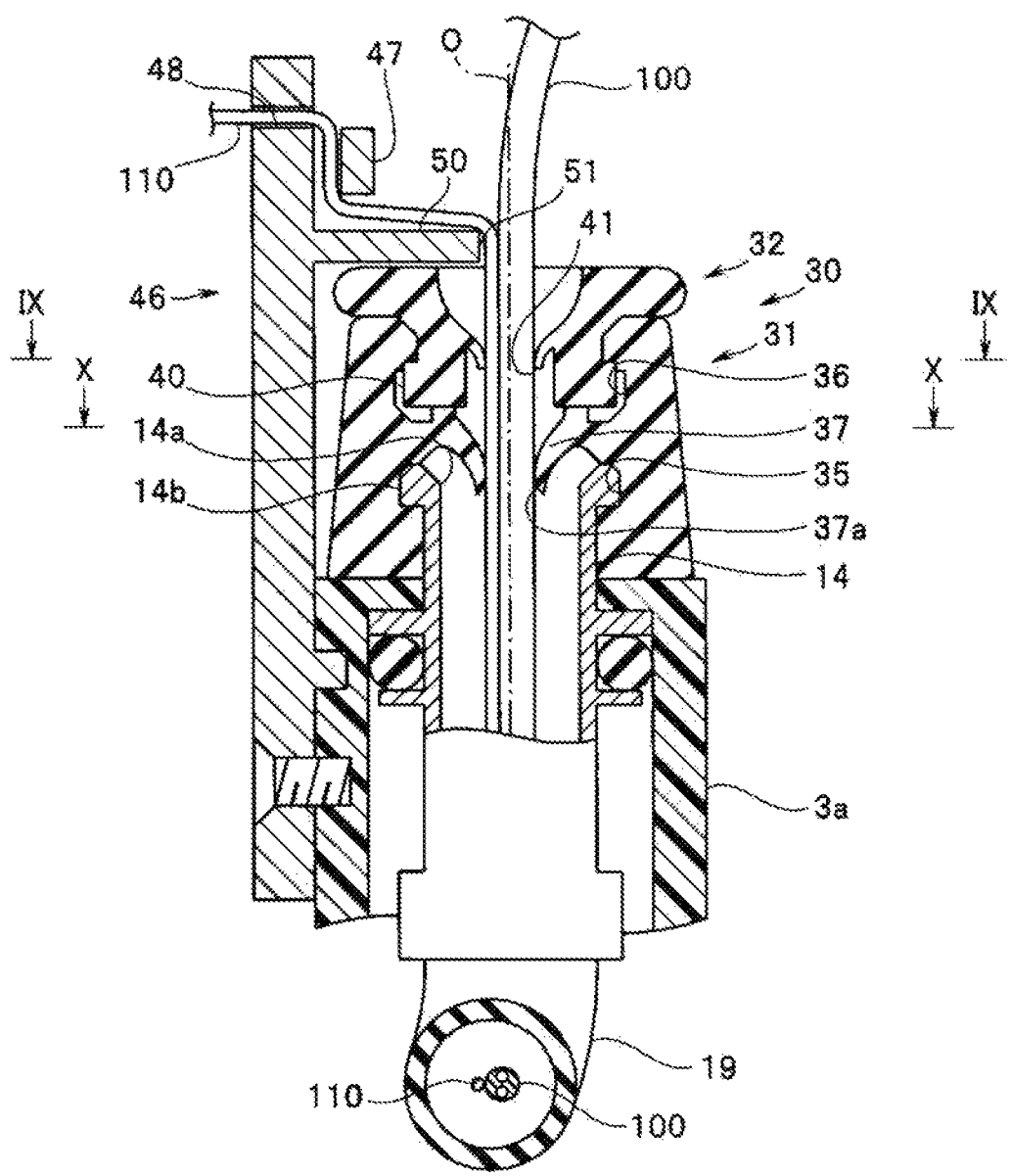
FIG. 7 is a cross-sectional view depicting the manner in which the guide wire projecting from the forceps plug is secured to the wire attaching member.
Figure 8:
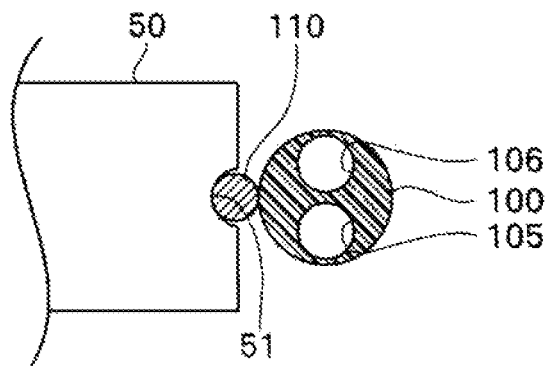
FIG. 8 is a plan view depicting a portion of a guide piece.

As depicted in FIGS. 3 and 4, for example, the attaching device 46 includes a hook-shaped first engaging member 47 and tortuously-shaped second engaging members 48. As depicted in FIGS. 5 and 7, for example, the guide wire 110 projecting from the forceps plug 30 can be attached longitudinally immovably to the attaching device 46 by engaging the first engaging member 47 and one of the second engaging members 48 successively. A portion of the guide wire 110 is positioned immediately after projecting from the forceps plug 30. In order to control a direction along which the portion of the guide wire 110 extends when the guide wire 110 is secured by engaging the engaging members 47 and 48, a guide piece 50 is located on the wire attaching member 45. The guide piece 50 is used as an instrument insertion assisting tool. The guide piece 50 includes a plate-shaped member projecting from the wire attaching member 45, for example, and has a protrusive end disposed in the vicinity of a central axis "O" of the slit 41 and the seal hole 37a.

The protrusive end of the guide piece 50 has an engaging cavity 51 in the form of a U-shaped groove engageable with the guide wire 110. The engaging cavity 51 is formed in the protrusive end along the central axis "O". A portion of the guide wire 110 is positioned immediately after projecting from the forceps plug 30 and before engaging the attaching device 46. The guide piece 50 is capable of causing the portion of the guide wire 110 to extend in a direction along the central axis "O" by having the guide wire 110 engage in the engaging cavity 51. In other words, the guide piece 50 can partly prevent the portion of the guide wire 110 from extending in the direction of the attaching device 46, i.e., from extending the shortest distance linearly in the direction of the attaching device 46.

According to the present embodiment, the instrument insertion assisting tool includes the forceps plug 30, the wire attaching member 45 and the guide piece 50.

The wire attaching member 45 secures the guide wire 110 at a position offset from the central axis "O" of the forceps plug 30. The guide piece 50 prevents a portion of the guide wire 110 from extending in the direction of the wire attaching member 45. The portion of the guide wire 110 is positioned immediately after projecting from the forceps plug 30. The guide piece 50 controls the portion of the guide wire 110 to extend along the central axis "O" of the slit 41 and the seal hole 37a. The guide wire 110 is thus appropriately secured on the manipulator 3 side while preventing a body fluid or the like from leaking out of the forceps plug 30.

Figure 9:
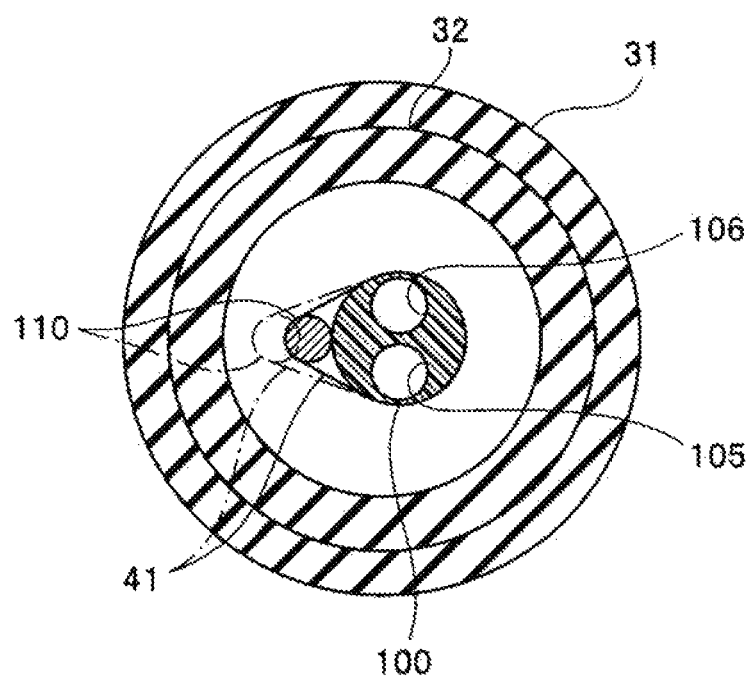
FIG. 9 is a cross-sectional view taken along line IX-IX of FIG. 7.
Figure 10:
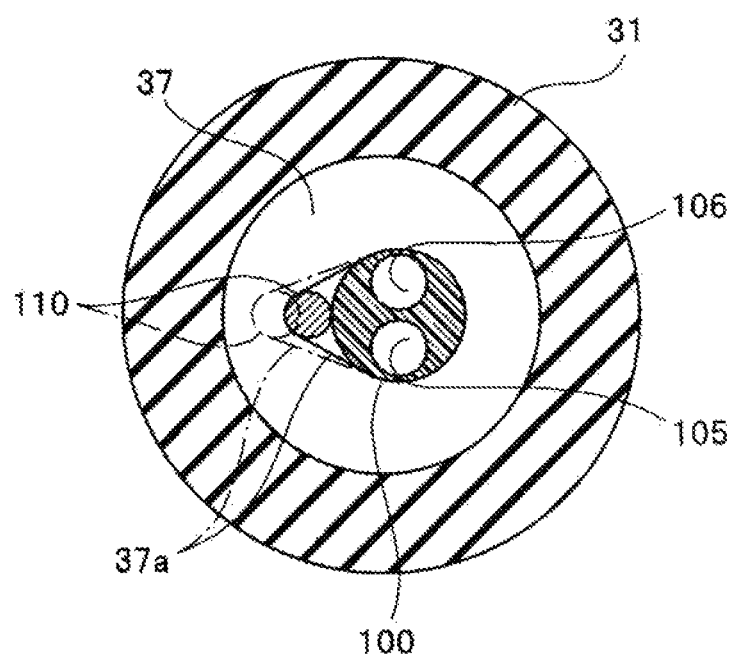
FIG. 10 is a cross-sectional view taken along line X-X of FIG. 7.

In other words, the direction in which the guide wire 110 extends is secured at a position offset from the central axis "O", however, the direction of the guide wire 110 is partly changed by the guide piece 50. The portion of the guide wire 110 is positioned immediately after projecting from the forceps plug 30. Therefore, the guide piece 50 prevents the portion of the guide wire 110 from developing a tensile force in other directions than the direction along the central axis "O". The guide wire 110 is thus prevented from unnecessarily elastically deforming and spreading open the slit 41 and the seal hole 37a, as depicted in FIGS. 9 and 10. In addition, the portion of the guide wire 110 which extends through the slit 41 and the seal hole 37a can extend without being spaced from the treatment instrument 100. Therefore, the slit 41 and the seal hole 37a are prevented from developing unwanted gaps, thereby appropriately preventing a body fluid or the like that has flowed into the treatment instrument channel 19 from leaking out through gaps in the slit 41 and the seal holes 37a. FIGS. 9 and 10 illustrate how the guide wire 110 behaves if the direction in which it extends is not controlled by the guide piece 50, as indicated by the dot-and-dash lines in a comparative example.

Figure 15:
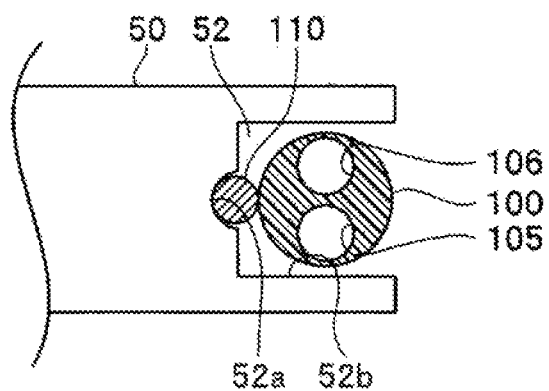
FIG. 15 is a plan view depicting a portion of a guide piece according to a second modification.

Various changes may be made with respect to the position where the guide piece 50 is disposed. For example, the guide piece 50 may be integrally formed with the lid 32 of the forceps plug 30, rather than with the wire attaching member 45. The structure thus modified offers the same operational features and advantages as those according to the above embodiment. Various changes may be made with respect to the shape of the engaging cavity. For example, as depicted in FIG. 15, an engaging cavity 52 may include a recess 52a and a recess 52b. The engaging cavity 52 is in the form of a U-shaped groove engageable with the guide wire 110. The recess 52b is in the form of a rectangular groove engageable with the treatment instrument 100. The recess 52b is integrally joined to a distal-end side of the recess 52a. With this arrangement, the engaging cavity 52 is also capable of defining the relative positions of the guide wire 110 and the treatment instrument 100, thereby more effectively preventing a body fluid or the like from leaking out of the slit 41 and the seal hole 37a.

Figure 16:
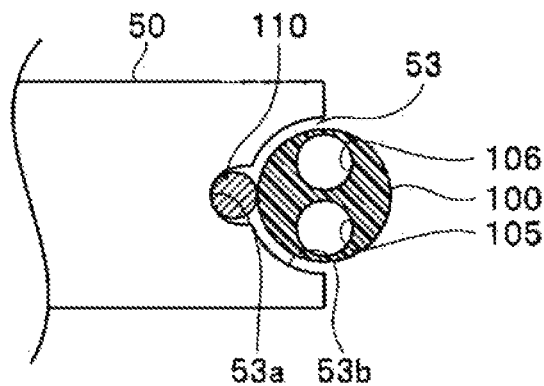
FIG. 16 is a plan view depicting a portion of a guide piece according to a third modification.
Figure 17:
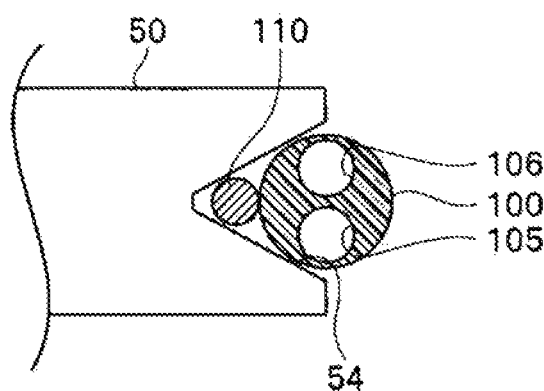
FIG. 17 is a plan view depicting a portion of a guide piece according to a fourth modification.
Figure 18:
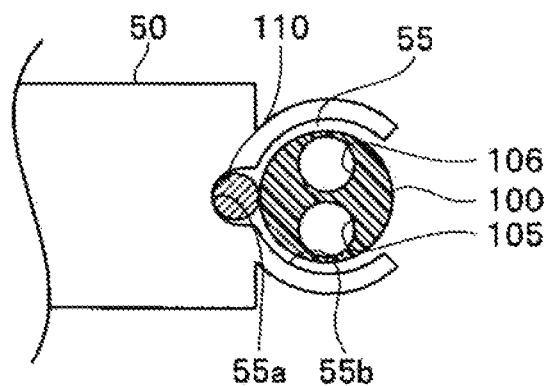
FIG. 18 is a plan view depicting a portion of a guide piece according to a fifth modification.

Furthermore, as depicted in FIG. 16, for example, an engaging cavity 53 may include a recess 53a and a recess 53b. The recess 53a is in the form of a U-shaped groove engageable with the guide wire 110. The recess 53b is in the form of a U-shaped groove engageable with the treatment instrument 100. The recess 53b is integrally joined to a distal-end side of the recess 53a. Moreover, as depicted in FIG. 17, for example, an engaging cavity 54 may include a recess in the form of a V-shaped groove engageable with the guide wire 110 and the treatment instrument 100. Furthermore, as depicted in FIG. 18, for example, an engaging cavity 55 may include a recess 55a and an elastic C-shaped recess 55b. The recess 55a is in the form of a U-shaped groove engageable with the guide wire 110. The elastic C-shaped recess 55b is engageable with the treatment instrument 100. The elastic C-shaped recess 55b is integrally joined to a distal-end side of the recess 55a.

Figure 19:
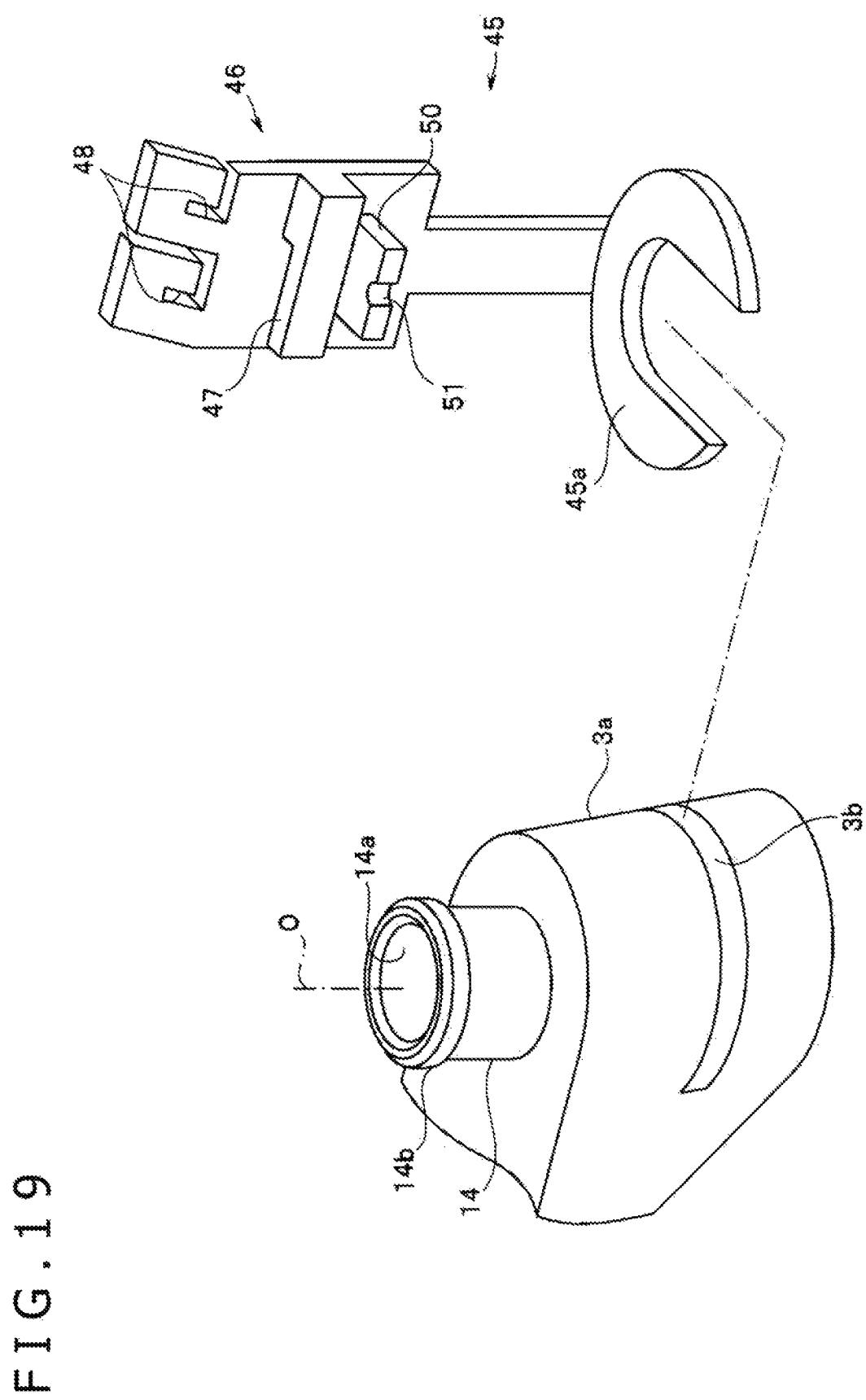
FIG. 19 is a perspective view depicting a wire attaching member according to a sixth modification before it is mounted on an endoscope.
Figure 20:
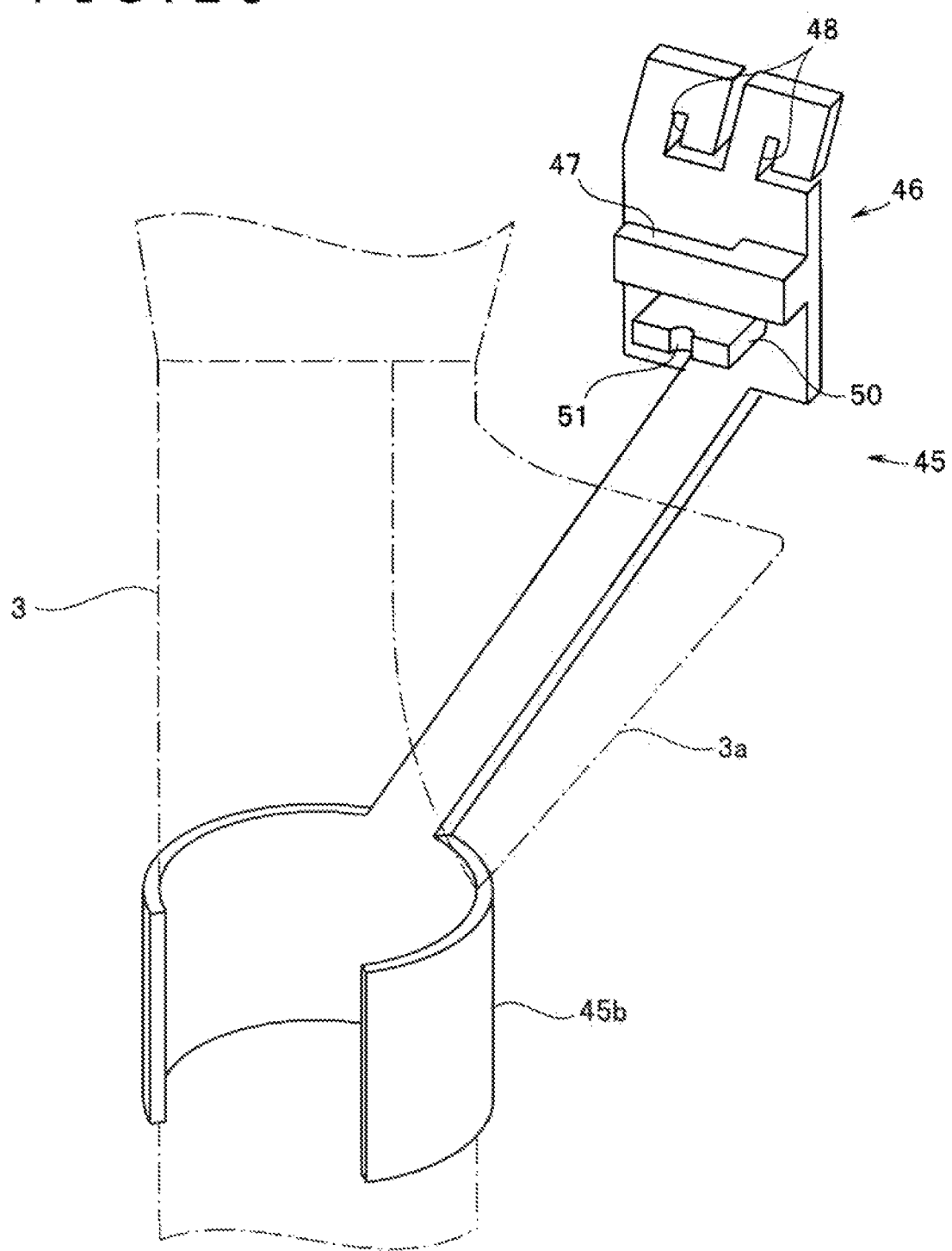
FIG. 20 is a perspective view depicting a wire attaching member according to a seventh modification.

Various modifications may also be made with respect to the structure by which the wire attaching member 45 is mounted on the endoscope 1. For example, as depicted in FIG. 19, the mount 3a may have a slit 3b defined therein, and the other end of the wire attaching member 45 may have a base 45a that can be fitted in the slit 3b. The wire attaching member 45 may be mounted on the endoscope 1 by fitting the base 45a in the slit 3b. Furthermore, as depicted in FIG. 20, for example, the other end of the wire attaching member 45 may have a C ring-shaped hook 45b. The wire attaching member 45 may be mounted on the endoscope 1 by elastically deforming the hook 45b into engagement with the manipulator 3.

In sum, one aspect of the technology disclosed herein is directed to an instrument insertion assisting tool for use with an endoscope including a tube through which an instrument and a guide wire used for guiding the instrument being inserted into an insertion portion. A forceps port through which the tube is open outwardly on a manipulator and a forceps plug mounted on the forceps port in closing relation thereto and having a hole through which the instrument and the guide wire extends. The instrument insertion assisting tool comprises a plate-shaped wire attaching member attached to the manipulator of the endoscope at a position adjacent to the forceps plug and offset from the hole. A plate-shaped guide piece is projected from the wire attaching member for partially controlling a direction along which the guide wire projecting from the forceps plug extends to cause a portion of the guide wire that is positioned immediately after projecting from the forceps plug to extend along a central axis of the hole. A hook-shaped first engaging member is projected from the wire attaching member for engaging the guide wire which extends along the direction controlled by the guide piece. A tortuously-shaped second engaging member for engaging another portion of the guide wire which is engaged by the first engaging member.

The guide piece has an engaging cavity defined therein which is engageable with the guide wire. The engaging cavity is engageable with the guide wire and the instrument insertion assisting tool integrally attached to one another.

An instrument insertion assisting tool comprises a wire attaching member configured to be attached to a manipulator of an endoscope at a position adjacent to a forceps plug and offset from a seal hole of the forceps plug. The forceps plug is attached to a forceps port of the manipulator and having the seal hole through which a wire is inserted. A guide piece is projected outwardly from the wire attaching member. The guide piece is configured to direct the wire so that a first portion of the wire is directed along a central axis of the seal hole. A first engaging member is projected outwardly from the wire attaching member. The first engaging member is configured to direct the wire so that a second portion of the wire is directed along the wire attaching member.

The instrument insertion assisting tool further comprises a second engaging member configured to direct the wire so that a third portion of the wire is guided along the wire attaching member. The second engaging member is formed in tortuously shape. The first engaging member is configured to direct the wire so that a fourth portion of the wire is directed along a direction perpendicular to the central axis. The fourth portion is located between the first portion and the second portion. The first engaging member is configured to direct the wire so that the second portion of the wire is directed along a direction parallel to the central axis. The second engaging member is configured to direct the wire so that the third portion of the wire is directed along a direction perpendicular to the central axis. The first engaging member is configured to direct the wire so that a fourth portion of the wire is directed along a direction perpendicular to the central axis. The fourth portion is located between the first portion and the second portion. The first engaging member is configured to direct the wire so that the second portion of the wire is directed along a direction parallel to the central axis.

The first engaging member includes a surface configured to contact with the wire. The surface is located so that a distance between the surface and the wire attaching member is shorter that a distance between the central axis and the wire attaching member. The surface is formed in flat shape. The second engaging member includes a flat-shaped surface configured to contact with the wire. The surface is perpendicular to the central axis. The instrument insertion assisting tool is attached to the manipulator of the endoscope. The endoscope includes a tube, the forceps port and an insertion portion. An instrument and the wire for guiding the instrument is inserted into the insertion portion through the tube. The tube is opened outwardly on a manipulator through the forceps port. The guide piece has an engaging cavity defined therein which is engageable with the wire. The guide piece has an engaging cavity defined therein which is engageable with the wire and the engaging cavity is engageable with the wire and the instrument integrally together. The wire attaching member includes a base configured to be fitted in a slit of the manipulator. The wire attaching member includes a ring-shaped hook configured to be attached to the manipulator.

The present disclosure is not limited to the embodiment described hereinbefore, but various changes and modifications may be made therein as falling within the technical scope of the invention. For example, the above embodiment and modifications may be combined in appropriate combinations.

What is claimed is:

1. An instrument insertion assisting tool for use with an endoscope including a tube through which a treatment instrument and a guide wire used for guiding the treatment instrument being inserted into an insertion portion, a forceps port through which the tube is open outwardly on a manipulator, and a forceps plug mounted on the forceps port in closing relation thereto, the forceps plug including a hole and a slit through which the instrument and the guide wire extends, the instrument insertion assisting tool comprising:
   a plate-shaped wire attaching member configured to attach to the manipulator of the endoscope at a position adjacent to the forceps plug and offset from the hole;
   a plate-shaped guide piece projecting from the wire attaching member for partially controlling a direction along which the guide wire projecting from the forceps plug extends to cause a portion of the guide wire that is positioned immediately after projecting from the forceps plug to extend along a central axis of the hole, the guide piece including a protrusive end that includes an engaging cavity formed in a u-shape on an outermost edge of the protrusive end, the outermost edge of the protrusive end being configured to extend to a center axis of the slit of the forceps plug;
   a hook-shaped first engaging member projecting from the wire attaching member for engaging the guide wire which extends along the direction controlled by the guide piece; and
   second engaging member formed in a tortuous shape configured to engage another portion of the guide wire which is engaged by the first engaging member.

2. The instrument insertion assisting tool of claim 1, wherein the engaging cavity is engageable with the guide wire and the treatment instrument integrally attached to one another.

3. The instrument insertion assisting tool of claim 1, wherein the engaging cavity is formed along the central axis of the hole.

4. An instrument insertion assisting tool comprising:
   a plate-shaped wire attaching member configured to attach to a manipulator of an endoscope at a position adjacent to a forceps plug and offset from a seal hole of the forceps plug, the forceps plug being attached to a forceps port of the manipulator and having the seal hole and through which a wire is inserted;
   a plate-shaped guide piece projecting from the wire attaching member, the guide piece configured to direct the wire so that a first portion of the wire is directed along a central axis of the seal hole, the guide piece including a protrusive end that includes an engaging cavity formed in a u-shape on an outermost edge of the protrusive end, the outermost edge of the protrusive end being configured to extend to a center axis of the seal hole of the forceps plug; and
   a first hook-shaped engaging member projecting from the wire attaching member, the first engaging member configured to direct the wire so that a second portion of the wire is directed along the wire attaching member.

5. The instrument insertion assisting tool of claim 4, further comprising: a second engaging member formed in a tortuous shape configured to direct the wire so that a third portion of the wire is guided along the wire attaching member.

6. The instrument insertion assisting tool of claim 5, wherein the second engaging member is configured to direct the wire so that the third portion of the wire is directed along a direction perpendicular to the central axis.

7. The instrument insertion assisting tool of claim 6, wherein the first engaging member is configured to direct the wire so that a fourth portion of the wire is directed along a direction perpendicular to the central axis, the fourth portion is located between the first portion and the second portion.

8. The instrument insertion assisting tool of claim 6, wherein the first engaging member is configured to direct the wire so that the second portion of the wire is directed along a direction parallel to the central axis.

9. The instrument insertion assisting tool of claim 5, wherein the second engaging member includes a surface configured to contact with the wire, the surface being in flat shape.

10. The instrument insertion assisting tool of claim 9, wherein the surface is perpendicular to the central axis.

11. The instrument insertion assisting tool of claim 4, wherein the first engaging member is configured to direct the wire so that a fourth portion of the wire is directed along a direction perpendicular to the central axis, the fourth portion is located between the first portion and the second portion.

12. The instrument insertion assisting tool of claim 4, wherein the first engaging member is configured to direct the wire so that the second portion of the wire is directed along a direction parallel to the central axis.

13. The instrument insertion assisting tool of claim 4, wherein the first engaging member includes a surface configured to contact with the wire, the surface being located so that a distance between the surface and the wire attaching member is shorter that a distance between the central axis and the wire attaching member.

14. The instrument insertion assisting tool of claim 13, wherein the surface is formed in flat shape.

15. The instrument insertion assisting tool of claim 4, wherein the instrument insertion assisting tool is attached to the manipulator of the endoscope, the endoscope includes a tube, the forceps port and an insertion portion, a treatment instrument and the wire for guiding the instrument being inserted into the insertion portion through the tube, the tube is opened outwardly on a manipulator through the forceps port.

16. The instrument insertion assisting tool of claim 4, wherein the wire attaching member includes a base configured to be fitted in a slit of the manipulator.

17. The instrument insertion assisting tool of claim 4, wherein the wire attaching member includes a ring-shaped hook configured to be attached to the manipulator.

* * * * *